(12) United States Patent
Smyth et al.

(10) Patent No.: US 7,918,781 B1
(45) Date of Patent: Apr. 5, 2011

(54) SYSTEMS AND METHODS FOR SUPPRESSING MOTION SICKNESS

(75) Inventors: Christopher C. Smyth, Fallston, MD (US); David C. Smyth, Baltimore, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 1414 days.

(21) Appl. No.: 11/387,079

(22) Filed: Mar. 22, 2006

(51) Int. Cl.
*A61M 21/00* (2006.01)
(52) U.S. Cl. .......................................................... 600/27
(58) Field of Classification Search ............... 600/26–28
See application file for complete search history.

(56) References Cited

U.S. PATENT DOCUMENTS

| | | | |
|---|---|---|---|
| 5,829,446 A * | 11/1998 | Tiffany | 128/898 |
| 5,966,680 A | 10/1999 | Butnaru | |
| 6,443,913 B1 | 9/2002 | Kania | |
| 6,497,649 B2 * | 12/2002 | Parker et al. | 600/27 |
| 2004/0100419 A1 * | 5/2004 | Kato et al. | 345/7 |
| 2004/0102676 A1 * | 5/2004 | Brendley et al. | 600/27 |
| 2006/0079729 A1 * | 4/2006 | Kim | 600/21 |

* cited by examiner

*Primary Examiner* — Charles A Marmor, II
*Assistant Examiner* — Catherine E. Burk
(74) *Attorney, Agent, or Firm* — Edward L. Stolarun; Avrom David Spevack (57) ABSTRACT

Systems for suppressing motion sickness are provided. In this regard, an exemplary system comprises a display device and a display controller. The display device is operative to display a first image and a second image. The display controller communicates with the display device and is operative to control display of the second image such that the second image moves relative to the display device in response to at least one of: motion of the first image relative to the display device, and motion of the display device. Methods and other systems also are provided.

18 Claims, 8 Drawing Sheets

---

DETERMINE MOTION OF FIRST IMAGE DISPLAYED IN SCENE FIELD OF A DISPLAY DEVICE    190

↓

DETERMINE MOTION OF AN OPERATOR VIEWING THE DISPLAY DEVICE    192

↓

DISPLAY SECOND IMAGE TO THE OPERATOR TO COMPENSATE FOR A DIFFERENCE BETWEEN THE MOTION OF THE FIRST IMAGE AND THE MOTION OF THE OPERATOR    194

SYSTEMS AND METHODS FOR SUPPRESSING MOTION SICKNESS

GOVERNMENT INTEREST

The invention described herein may be manufactured, used, and licensed by or for the United States Government.

BACKGROUND

1. Technical Field

The present invention generally relates to the suppression of motion sickness in human operators viewing display devices.

2. Description of the Related Art

Motion sickness is provoked by sensory conflict between visual and sensory-motor activities that involve the vestibular system through head movements. Associated with motion sickness is a constellation of autonomic symptoms such as pallor, drowsiness, salivation, sweating, nausea and, in more severe cases, vomiting. Although some individuals eventually adapt to situations that initially provoke such sickness, others do not. In these individuals, occurrences may be severe enough to arrest task performance until the symptoms subside.

Figure 1:
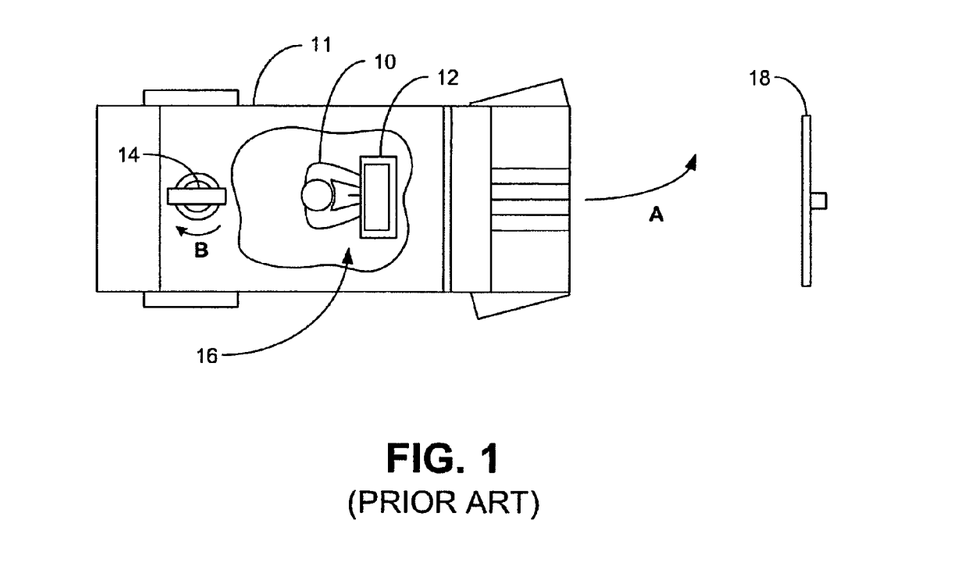
FIG. 1 is a schematic diagram depicting a vehicle in which a human operator and display device are located.

In field experiments conducted by the U.S. Army Research Laboratory on indirect vision driving, some symptoms of motion sickness occurred in most of the participants. As shown in FIG. 1, participants, such as operator 10, drove a ground vehicle 11, while viewing a vehicle-mounted display 12. The display provided the participants with images of the external scene return from a forward-looking camera 14 mounted on the exterior of the vehicle. The cab area 16 was completely enclosed to prevent direct viewing of the external scene by the participants. On average, one out of eight participants was made sick enough to abort the driving task.

In other experiments, participants have reported symptoms of motion sickness while operating a movable camera, e.g., a camera mounted on a remote vehicle, from inside a moving control vehicle. Symptoms of motion sickness can be particularly strong when the control vehicle is turning in a direction opposite to the direction of turn of the camera. In such a case, the motion of the scene viewed on the display is directly opposite to that sensed by the vestibular system of the human operator riding in the control vehicle.

Figure 2A:
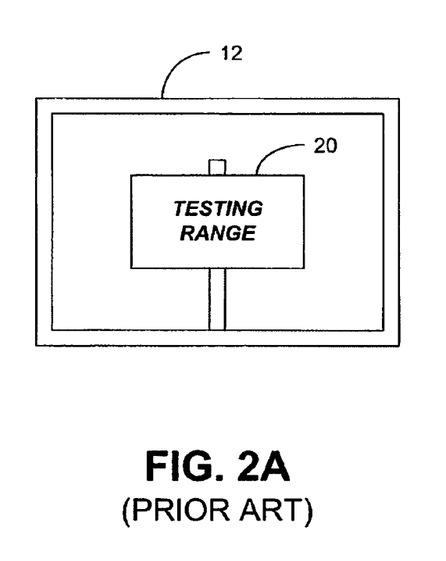
FIGS. 2A and 2B are schematic diagrams depicting representative images provided by the display device of FIG. 1.
Figure 2B:
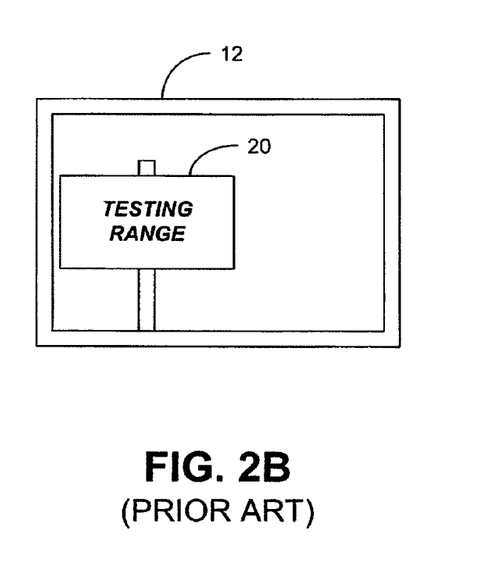

With respect to the example previously provided in FIG. 1, if the vehicle 11 is turning as indicated by arrow A and the camera 14 is simultaneously rotated clockwise at a rate of turn greater than that of the vehicle (arrow B), the sequential images of the exterior scene displayed to the user are as shown in FIGS. 2A and 2B. That is, the image 20 associated with the exterior scene, e.g., the sign 18, is displayed to the operator as moving to the left across the display device 12. Since an operator is accustomed to an exterior scene moving to the right when the vehicle in which the operator is located is turning to the left, motion sickness can be induced in the operator.

SUMMARY

Systems and methods for suppressing motion sickness are provided. In this regard, an embodiment of a system comprises a display device and a display controller. The display device is operative to display a first image and a second image. The display controller communicates with the display device and is operative to control display of the second image such that the second image moves relative to the display device in response to at least one of: motion of the first image relative to the display device, and motion of the display device.

Another embodiment of a system comprises a display device, a display controller, an image motion sensor and a display motion sensor. The display device has a scene field for displaying scene images and a compensatory field for displaying compensatory images, with the compensatory field being of two components, one component being located about the periphery or border of the scene field, and the second component being superimposed over the scene field. The display controller communicates with the display device and is operative to control display of the compensatory images. The image motion sensor is operative to determine motion of the scene images relative to the display device, with the image motion sensor providing information corresponding to motion of the scene images to the display controller. The display motion sensor is operative to determine motion of the display device, with the display motion sensor providing information corresponding to the motion of the display device to the display controller. The display controller receives the information from the image motion sensor and the display motion sensor, and controls the display device such that the compensatory images move, with respect to the display device, in a manner correlated to the motion of the scene images and the motion of the display device.

An embodiment of a method for suppressing motion sickness in an operator of a display device, wherein the display device displays a first image, comprises: displaying a second image to the user, the second image moving relative to the display device in a manner corresponding to at least one of: motion of the first image relative to the display device, and motion of the display device.

Other systems, methods, features and/or advantages will be or may become apparent to one with skill in the art upon examination of the following drawings and detailed description. It is intended that all such additional systems, methods, features and/or advantages be included within this description and be protected by the accompanying claims.

BRIEF DESCRIPTION OF THE DRAWINGS

The components in the drawings are not necessarily to scale relative to each other. Like reference numerals designate corresponding parts throughout the several views.

DETAILED DESCRIPTION

As will be described in detail herein, systems and methods are provided that can potentially suppress motion sickness in an operator who is viewing a scene, e.g., the scene return from a video camera, displayed by a display device. Specifically, compensatory images are displayed to the operator to compensate for the displayed scene that is causing the motion sickness. The compensatory images are controlled to correspond to changes in the velocity flow of the displayed scene, as well as to accelerations sensed by the operator viewing the displayed scene. As used herein, "velocity flow" refers to the direction and speed of motion of an image with respect to the display device that is used to display the image.

With brief reference again to FIG. 1, recall that the operator 10 is located within a vehicle 11 in which a display device 12 is mounted. The camera 14 associated with the vehicle acquires image data corresponding to an exterior scene. In FIG. 1, the camera is acquiring images associated with a sign 18.

Recall also that the vehicle 11 is turning to the left while the camera 14 is rotating clockwise at a rate that is greater than the turn rate of the vehicle. Therefore, the images from the camera that are displayed by the display device (FIGS. 2A and 2B) do not correspond to the sensory-motor cues sensed by the vestibular system of the operator.

Figure 3A:
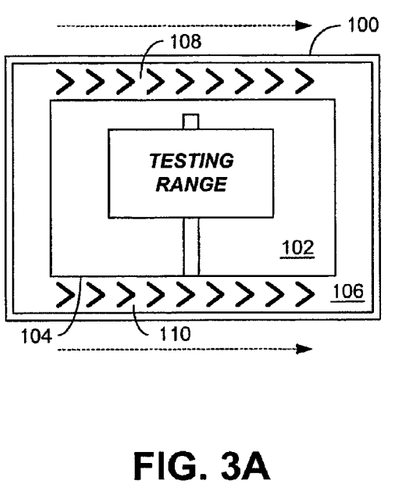
FIGS. 3A and 3B are schematic diagrams depicting images provided by an embodiment of a system for suppressing motion sickness.
Figure 3B:
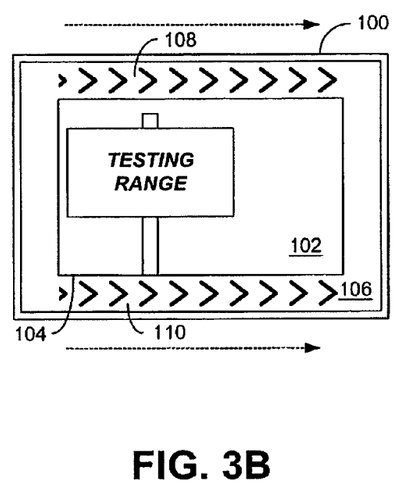

FIGS. 3A and 3B schematically depict images displayed by a display device of an embodiment of a system for suppressing motion sickness when operating in the scenario of FIG. 1. Specifically, as shown in FIG. 3A, display device 100 includes a scene field 102 that is used for displaying images acquired by a video camera, e.g., camera 14 of FIG. 1. Outside the periphery 104 of the scene field is a compensatory field 106 that displays additional images, i.e., compensatory images. In this case, two patterns 108,110 of compensatory images are displayed, with pattern 108 being displayed above the scene field and pattern 110 being displayed below the scene field. The compensatory images of each pattern move across the compensatory field 106 in a direction and speed that is counter to that of the images being displayed within the scene field 102. Note that in comparing FIG. 3B to FIG. 3A, the chevrons have moved to the right, with new chevrons forming at the left side of the display device. The net effect is that the combined movement of the compensatory images and the scene images displayed to the operator more closely correspond to the accelerations sensed by the operator.

Figure 4:
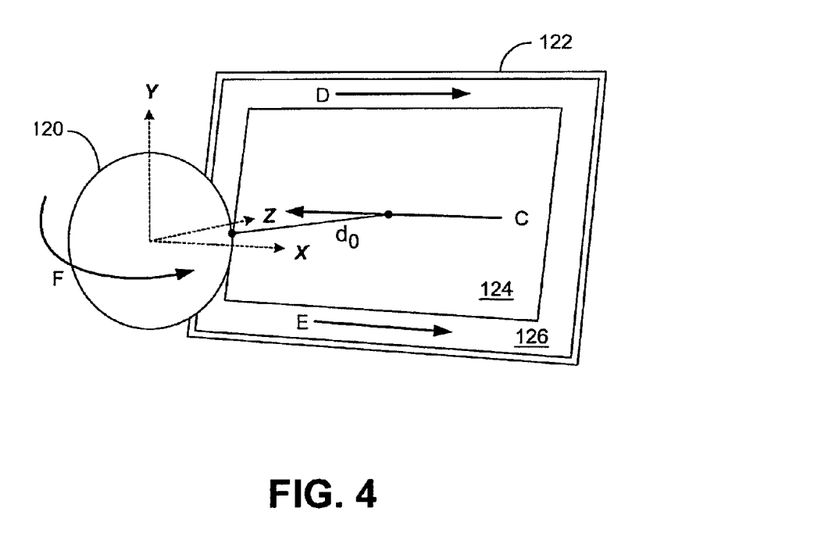
FIG. 4 is a schematic diagram of an operator viewing an embodiment of a display device of a system for suppressing motion sickness.

FIG. 4 schematically depicts the relationship between an operator viewing an embodiment of a display device and the scene and compensatory fields of that display device. Specifically, FIG. 4 depicts an operator 120 viewing a display device 122 from a viewing distance $d_o$. Display device 122 includes a scene field 124, which is displaying scene images that are moving to the left (indicated by arrow C), and a compensatory field 126, which is displaying compensatory images that are moving to the right (indicated by arrows D and E).

Consider first this effect in a low resolution display such as a scrolling text file, where the movements are naturally interpreted by the display operator as scene rotations. Now, let $V_O$ be the stable earth referenced scene velocity flow, i.e., the velocity flow of images displayed to the operator that corresponds to the motion (indicated by arrow F) sensed by the operator; let $V_S$ be the velocity flow of images displayed in the scene field 124; and let $V_C$ be the velocity flow of images displayed in the compensatory field 126. Then, $V_C = V_S - V_O$.

The accelerations experienced by the operator are determined with respect to an arbitrary coordinate system 120 that has an x-axis parallel to the x-axis of display device 122 and a y-axis that is parallel to the y-axis of the display device. Therefore, with respect to the motion of the operator relative to the x-axis of coordinate system 120, the acceleration of the operator is expressed as $\alpha_X$. The x-axis component of the stable scene velocity flow ($V_{OX}$) is represented by $V_{OX} = (\alpha_X * d_o)^{1/2}$. Then, with $V_{SX}$ being the x-axis component for the velocity flow of images displayed in the scene field, the x-axis component of the velocity flow of images displayed in the horizontal compensatory field ($V_{CX}$) is given by $V_{CX} = V_{SX} - (\alpha_X * d_o)^{1/2}$.

Similarly, with respect to the motion of the operator relative to the y-axis of coordinate system 120, the acceleration of the operator is expressed as $\alpha_Y$. The y-axis component of the stable scene velocity flow ($V_{OY}$) is represented by $V_{OY} = (\alpha_Y * d_o)^{1/2}$. Then, with $V_{SY}$ being the y-axis component for velocity flow of images displayed in the scene field, the y-axis component of the velocity flow of images displayed in the (vertical side) compensatory field ($V_{CY}$) is given by $V_{CY} = V_{SY} - (\alpha_Y * d_o)^{1/2}$.

Note that, for those embodiments that consider the z-axis motion, $V_{CZ} = V_{SZ} - (\alpha_Z * d_o)^{1/2}$. By way of example, one manner to display compensatory images that vary in response to motion along the z-axis is to change the size of the compensatory images so that the images appear to get closer or move farther away from the operator. While this analysis is limited to rotations, as shall be demonstrated below, similar comments apply to linear motions.

Based on these equations, there is no velocity flow for images displayed in the compensatory field when images displayed in the scene field are moving in a direction and at a rate opposite to those of the direction and rate of the vehicle in which the operator is located. In contrast, images displayed in the scene field that are moving in the same direction as the vehicle result in an opposing velocity flow of the images displayed in the compensatory field.

In order to provide suitable compensatory images, measurements of the velocity flows of the images displayed in the scene field as well as the acceleration experienced by the operator should be real-time and accurate. In some embodiments, the velocity flow field of the images displayed in the scene field can be estimated from analysis of the images themselves. For instance, the position of a particular object displayed in the scene field can be determined periodically for measuring the velocity flow. Additionally or alternatively, information corresponding to the position, orientation and/or speed of the vehicle on which the camera that is acquiring the images for display in the scene field can be used. In the case of teleoperations, such information could be extracted from the control signals used to control the vehicle and/or camera.

The accelerations experienced by the operator can be measured by one or more sensors, e.g., accelerometers, that can be mounted in various locations. For instance, one or more sensors can be located on the display device, on the vehicle body and/or on the operator, e.g., on the operator's helmet.

Figure 5:
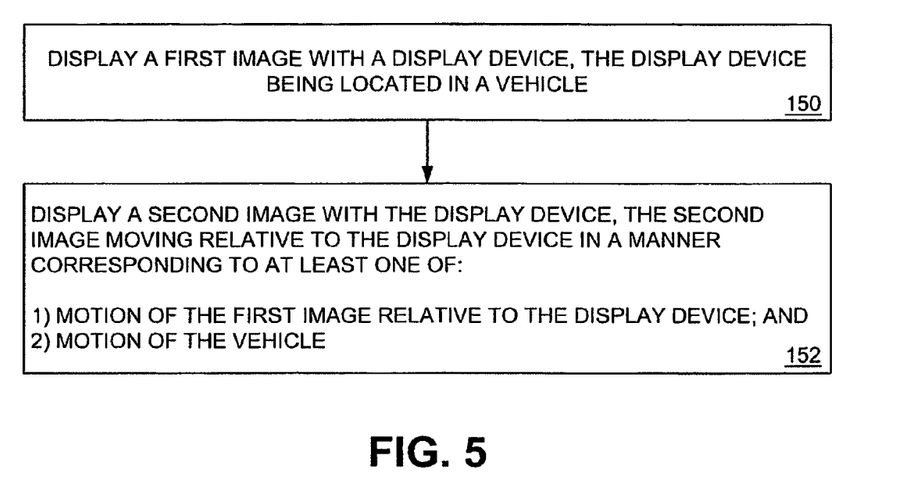
FIG. 5 is a flowchart depicting functionality of an embodiment of a system for suppressing motion sickness.

FIG. 5 is a flowchart depicting functionality of an embodiment of a system for suppressing motion sickness. As depicted in FIG. 5, the functionality (or method) may be construed as beginning at block 150, where a first image is displayed with a display device. Specifically, the display device is located in a vehicle. In block 152, a second image is displayed with the display device. In particular, the second image is displayed to move relative to the display device in a manner corresponding to at least one of: motion of the first image relative to the display device; and motion of the vehicle.

Having now described several embodiments in general, additional embodiments of systems and methods for suppressing motion sickness will now be described in greater detail. It should be noted that embodiments of such systems can be implemented in software, firmware, hardware, or combinations thereof. When implemented in hardware, such a system can be implemented with any or a combination of various technologies. By way of example, the following technologies, which are each well known in the art, can be used: a discrete logic circuit(s) having logic gates for implementing logic functions upon data signals, an application specific integrated circuit(s) (ASIC) having appropriate combinational logic gates, a programmable gate array(s) (PGA), and a field programmable gate array(s) (FPGA).

When implemented in software, such a system typically is used in conjunction with a computer or processor-based device. An example computer that can be used to implement an embodiment of a system for suppressing motion sickness is depicted schematically in FIG. 6.

Figure 6:
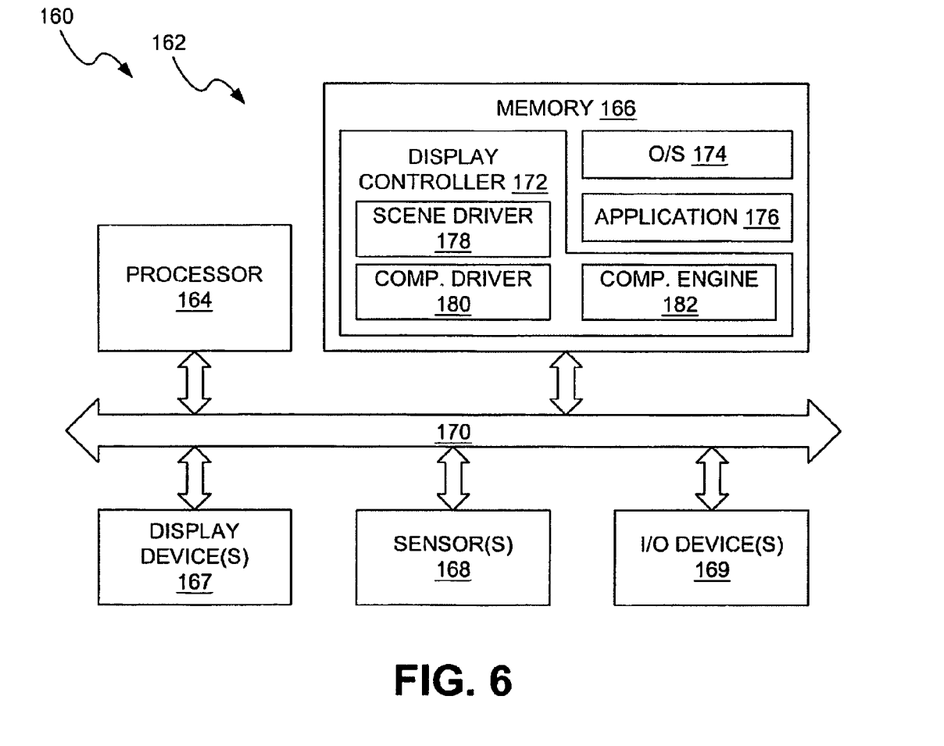
FIG. 6 is a schematic diagram of a computer or processor based device that can be used to implement an embodiment of a system for suppressing motion sickness.

As shown in FIG. 6, an embodiment of a system for suppressing motion sickness 160 includes a computer 162. Computer 162 incorporates a processor 164, memory 166, a display device 167, a sensor(s) 168, and an input and/or output (I/O) device(s) 169 that are communicatively coupled via a local interface 170. The software in memory 166 can include one or more separate programs, each of which comprises an ordered listing of executable instructions for implementing logical functions.

In the embodiment of FIG. 6, the software in the memory 166 includes a display controller 172, an operating system (O/S) 174, and an application 176 that provides an output to the display device. The display controller 172 includes a scene image driver 178, a compensatory image driver 180 and a compensatory image engine 182.

In operation, the display controller 172 provides information to the display device 167 for displaying scene images and compensatory images. Specifically, the scene images that are displayed in the scene field of the display device are controlled by the scene image driver 178, and the compensatory images that are displayed in the compensatory field are controlled by the compensatory image driver 180. The scene image driver 178 receives information for the application 176 and/or the I/O device(s) 169 that corresponds to the scene images. The scene image driver 178, in addition to providing an input for controlling the scene field, provides an input to the compensatory image engine 182. This input is used by the compensatory image engine to determine the velocity flow of the scene images. For instance, in this embodiment, consecutive positions of a selected scene image are analyzed to determine the velocity flow. Rotational velocities of the scene images are computed from the velocity flow and the distance of the display device from the viewing position of the operator. Thus, in this embodiment, the compensatory image engine functions as an image motion sensor.

The motion of the operator is determined by the sensor(s) 168, with information from the sensor(s) being provided to the compensatory image engine. The compensatory image engine then uses the various inputs to calculate parameters associated with compensatory images that are to be displayed within the compensatory field of the display device 167. Information corresponding to the parameters of the compensatory image is provided to the compensatory image driver 180, which then provides corresponding input to the display device for controlling the compensatory images.

In some embodiments, the compensatory image engine 182 can receive an input from the application 176 that corresponds to the state of the application. For example, operator inputs to the application can be analyzed for providing predictive control to the compensatory images.

Figure 7:
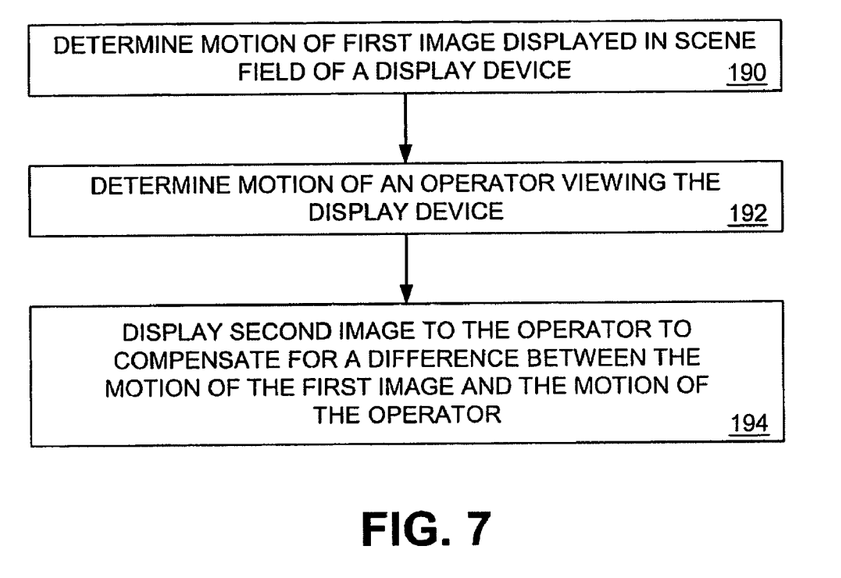
FIG. 7 is a flowchart depicting functionality of another embodiment of a system for suppressing motion sickness.

FIG. 7 is a flowchart depicting functionality of another embodiment of a system for suppressing motion sickness. It should be noted that, in some alternative implementations, the functions noted in the various blocks of this and/or other flowcharts depicted in the accompanying disclosure may occur out of the order depicted.

As shown in FIG. 7, the process may be construed as beginning at block 190, where the velocity of a first image displayed in a scene field of a display device is determined. In block 192, the acceleration experienced by an operator viewing the display device is determined. In block, 194, a second image is displayed to the operator to compensate for a difference between the velocity of the first image and the acceleration.

Figure 8:
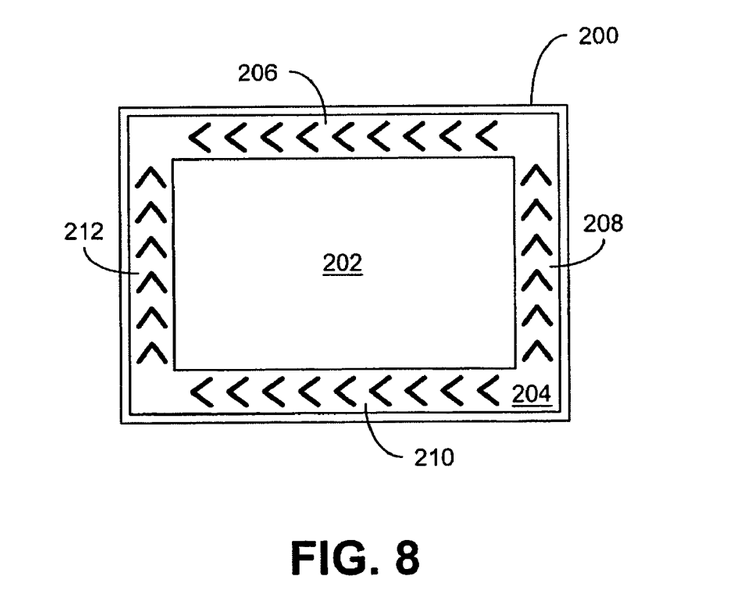
FIG. 8 is a schematic diagram of an embodiment of a display device depicting representative images for suppressing motion sickness.

FIG. 8 schematically depicts an embodiment of a display device 200 that is presently using chevrons as the compensatory images. Display device 200 includes a scene field 202 and a compensatory field 204. The compensatory field is divided into multiple frames, each of which displays a separate pattern of compensatory images. Specifically, display device 200 includes frames 206, 208, 210 and 212. In this case, the compensatory images are moving in the directions of the dashed arrows. That is, the chevrons displayed in the horizontal frames 206, 210 are moving to the left, and the chevrons displayed in the vertical frames 208, 212 are moving upward.

Figure 9:
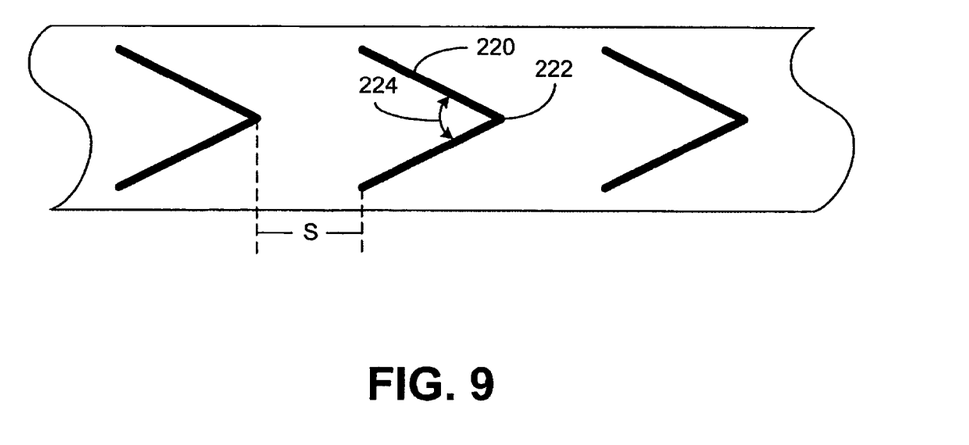
FIG. 9 is a schematic diagram depicting representative images for suppressing motion sickness.

Schematically depicted in FIG. 9 is a portion of a compensatory field frame in which is depicted several compensatory images. Specifically, each of the compensatory images is a chevron that includes an apex and an included angle. For instance, chevron 220 includes an apex 222 and an included angle 224. Although various shapes of compensatory images can be used, chevrons can be advantageous in several respects. For instance, the apex of the chevron can point in the direction of velocity flow, thereby enhancing the visual impact of the compensatory images. Additionally, as the velocity flow in a particular direction increases, the included angle can be decreased. Moreover, the spacing(s) between adjacent chevrons can be decreased as the velocity flow increases, thereby further enhancing the visual impression. Various other techniques can be used in addition to, or in lieu of, the previously mentioned techniques. For example, the thickness of a compensatory image can be increased as the velocity increases.

Figure 10:
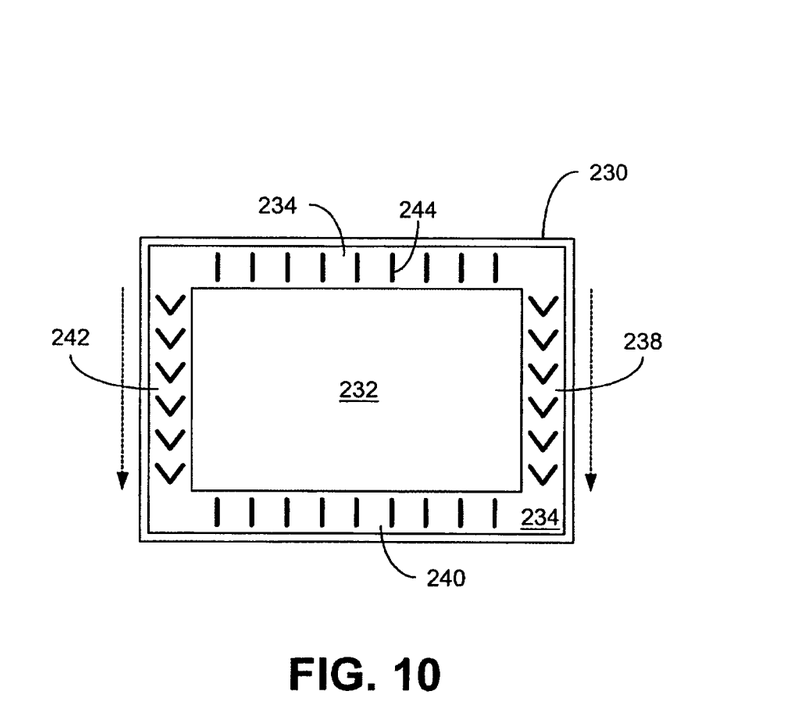
FIG. 10 is a schematic diagram of another embodiment of a display device depicting representative images for suppressing motion sickness.

FIG. 10 schematically depicts another embodiment of a display device 230 that includes a scene field 232 and surrounding compensatory field 234 that includes frames 236, 238, 240 and 242. Note that the horizontal frames 236, 240 are currently depicting static compensatory images. Specifically, the chevrons, e.g., chevron 244, displayed in the horizontal frames each have an included angle of 180 degrees, i.e., each is a line. This is representative of $V_{CX}$ being zero.

Figure 11:
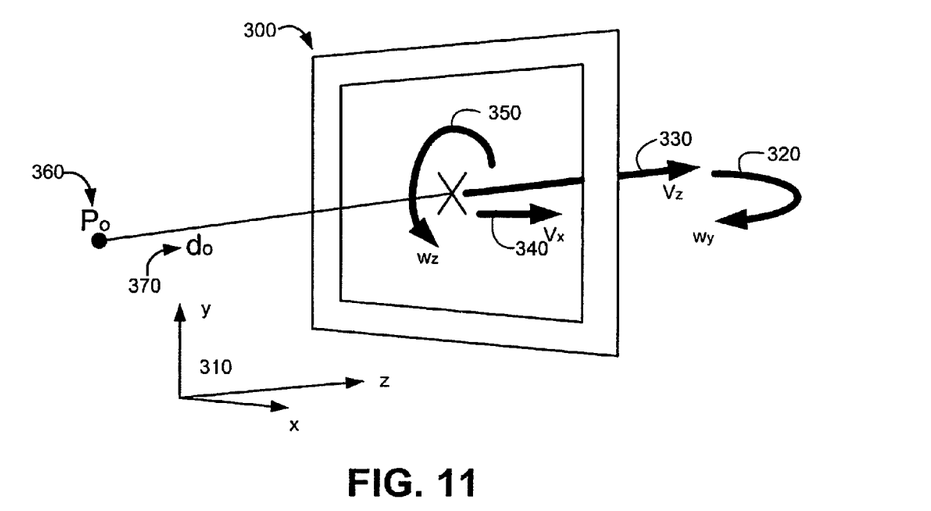
FIG. 11 is a diagram depicting the motion components of a display scene for a camera view.

Consider now the motions perceived on a high resolution display such as that for a camera scene from a moving vehicle. Here, the display operator has the resolution needed to discern the vehicle movements. Considering, in detail, the motions perceived on the display in a camera scene, FIG. 11 illustrates the velocity components that would be seen by the operator in an embodiment of these methods. The viewing point $P_o$ 360 of the operator is assumed to be a distance $d_o$ 370 from the display 300 that is equivalent to the camera focal point. Accordingly, the field of view that the operator sees for the display is the same as that subtended by the camera lens for the scene. Referring to the display coordinate system 310, the display scene can have several velocity components as the vehicle moves: a rotational velocity $\omega_y$ 320 about the y-axis that, for a fixed forward staring camera, corresponds to a turning (and pitch) effect; a linear forward z-axis velocity $V_z$ 330 along the turn; and a linear sideward x-axis velocity $V_x$ 340 from a skidding movement. In addition, there is a torque effect $\omega_z$ 350 about the z-axis in the display face from a roll in the turn. One of ordinary skill in the art will realize that other rotational and linear motions are possible using these methods. These velocities and the resulting accelerations are determined by the compensatory image engine from an analysis of the movements of matching scene elements.

Figure 12:
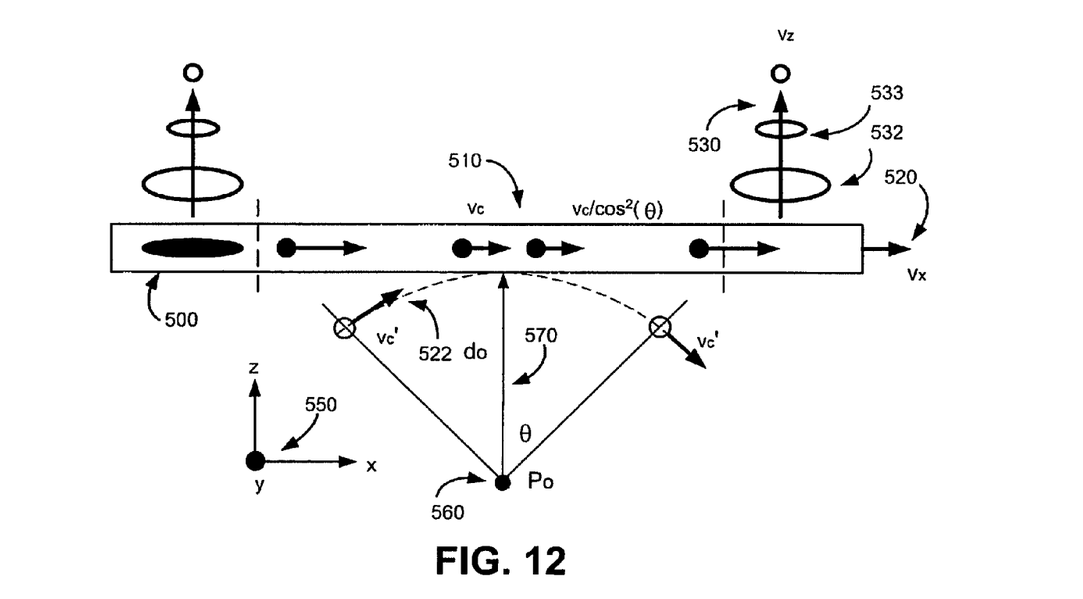
FIG. 12 is a top view of the movement fields of the images for suppressing motion sickness in a camera scene.

Reference is now made to FIG. 12, which depicts a top view of the movement fields of the images for suppressing motion sickness in a camera scene and specifically illustrates the velocity flow that would result from the compensatory display driver as determined from the image engine for the scene accelerations and those on the operator. For the purposes of illustration, only the velocity flow of the elements for the top horizontal compensatory display is shown. As in FIG. 11, the viewing point $P_o$ 560 of the operator is a distance $d_o$ 570 from the display 500. Additionally, the coordinate system 550 is consistent with that of FIG. 11. The figure shows a compensatory velocity $\upsilon_c'$ 522 about the y-axis in response to discrepancies in rotational acceleration 510, a linear velocity $\upsilon_z$ for forward acceleration 530, and linear velocity $\upsilon_x$ for sidewards accelerations 520. The solid vectors denote actual velocity flow and broken line vectors denote apparent velocity flow to the operator. Similarly, the compensatory elements are denoted as filled circles and the apparent elements by unfilled circles for simplicity.

Referring now to the rotational velocity 510 in FIG. 12. Where $\omega_y$ is the rotational velocity of the scene and $V_z$ is the forward velocity, the rotational acceleration is given by $\alpha_s = \omega_y * V_z$. Similarly, the display operator physically experiences a rotational acceleration, $a_o$, while riding in the vehicle during a turn. In a turn, the operator experiences a centripetal force applied by the seat belt harness forcing him or her to move in a curved path with the vehicle. This force causes the sensation of a virtual centrifugal acceleration. The discrepancy between the observed rotational acceleration on the display and that experienced by the operator is $a_{do} = a_o - \omega_y * V_z$. For a normal viewing distance, $d_o$, this corresponds to a velocity at the display compensatory field of $\upsilon_c = \text{sqrt}[(a_o - \omega_y V_z) * d_o]$, in the direction of the discrepancy.

Furthermore, as shown in FIG. 12 for a flat display surface the actual viewing distance varies with viewing offset angle, $\theta$, from the display normal and the corresponding compensatory velocity is $\upsilon_c / \cos^2(\theta)$, at this angle. That is, the velocity will be faster at the edges then in the center of the compensatory field to maintain the appearance of a rotational flow as seen from the operator's position. Further, as a consequence of the flow pattern, the display elements will be spread out at the edges and bunch together in the center as the flow occurs. In this way, the flow pattern on the flat display surface will appear to the operator as a compensatory rotation of equally spaced elements with velocity $\upsilon_c'$.

Reference is now made to the sideward accelerations 520. For example, $\alpha_x$ is the acceleration of the linear sideward velocity, $V_x$, of the scene on the display, and the operator experiences a sideward acceleration, $a_x$, in the vehicle. The discrepancy between the observed linear acceleration on the display and that experienced by the operator is $a_{dx} = a_x - \alpha_x$. The compensatory velocity flow must exhibit acceleration equal to and in the same direction as the discrepancy. Thus, the entire horizontal compensatory field moves at a linear velocity $\upsilon_x$ with the rotational compensation speeds superimposed, where the linear velocity referenced from zero has the acceleration, $a_{dx}$, that is, $\upsilon_x = (a_x - \alpha_x) * t$, where t is the time that the display element has been presented.

Referring now to the linear forward accelerations 530. The term $\alpha_z$ is the acceleration of the linear forward velocity $V_z$ of the scene on the display and the operator experiences a forward acceleration, $a_z$, in the vehicle. The discrepancy between the observed linear acceleration on the display and that experienced is $a_{dz} = a_z - \alpha_z$. The compensatory velocity flow must exhibit acceleration equal to and in the same direction as the discrepancy. One way of exhibiting this flow on the display is to show a compensatory element as either decreasing or increasing in size over time. FIG. 12 illustrates the apparent image generated by the vertical compensatory display elements 532-533 changing size at a rate corresponding to a linear velocity of travel $V_z$, where the linear velocity referenced from zero has the acceleration, $a_{dz}$. Thus, the size of the display element is given by the expression $r = r_o / (d_o + \frac{1}{2} * (a_z - \alpha_z) * t^2)$, where $r_o$ is a reference size scaled for the apparent perspective distance that would be reached with the forward velocity $\upsilon_z = (a_z - \alpha_z) * t$, and t is the time that the display element has been presented. Based on the assumption of consistency of object size, the perceived impression is either that of slowing down or speeding up. Observing a figure decreasing in size implies slowing down since the figure is flowing on past the observer, while a figure increasing in size implies speeding up since the figure is being approached for passing.

Figure 13:
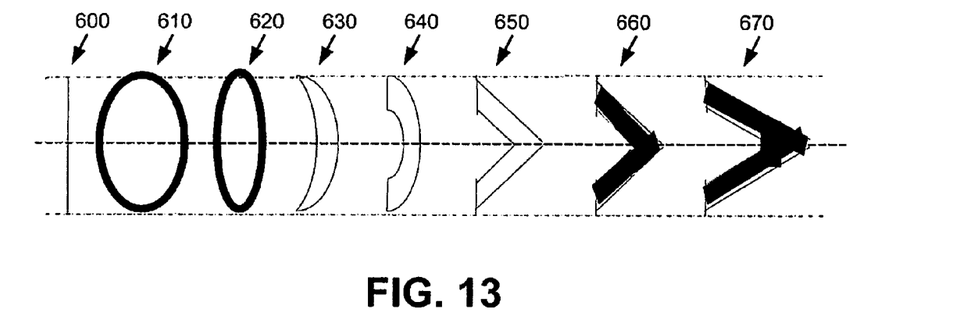
FIG. 13 is a diagram depicting the different compensatory display elements generated by morphologic variations of the element form.

In an exemplary embodiment, an expanded set of element features is used to support the increase in movement resolution. Here, since the display properties of the compensatory elements are features readily noticed with peripheral vision, the elements are simple geometrical shapes that appear to naturally morph from one to the other as the speed increases. FIG. 13 illustrates examples of several such figures: a line 600, circle 610, ellipse 620, cusp 630, sector 640, chevron 650, filled chevron 660, and filled chevron 670 with sharpen apex. One of ordinary skill in the art will know that many other shapes, figures and variations thereof could be used in these methods.

The line 600 indicates no movement, the circle 610 indicates movement either forward or back, the ellipse 620 indicates movement to the side as well as forward, and the cusp 630 and sector 640 are transient figures that lead to the chevron 650, which indicates side movement. In addition, color is used as another simple feature to indicate the direction of the acceleration with, say, the color red indicating acceleration and blue indicating deceleration. The color hue indicates the strength with the color magenta (sum of red and blue) indicating no acceleration.

The saturation intensity of the compensatory displays is a function of the power spectrum of the acceleration frequencies. Motion sickness is apparently related to the oscillatory changes in acceleration. The saturation intensity is most sensitive to the acceleration amplitudes in the frequency range that the human operator is most sensitive to motion sickness. This is commonly 0.1-0.5 Hertz. The intensity falls off on either side of this frequency range since outside of this range the compensatory display distracts from the scene. The intensity is reduced when the operator is not using the scene display; the lack of activity on the scene display concurrence with other activities acts as a dimmer-switch for the intensity.

Figure 14:
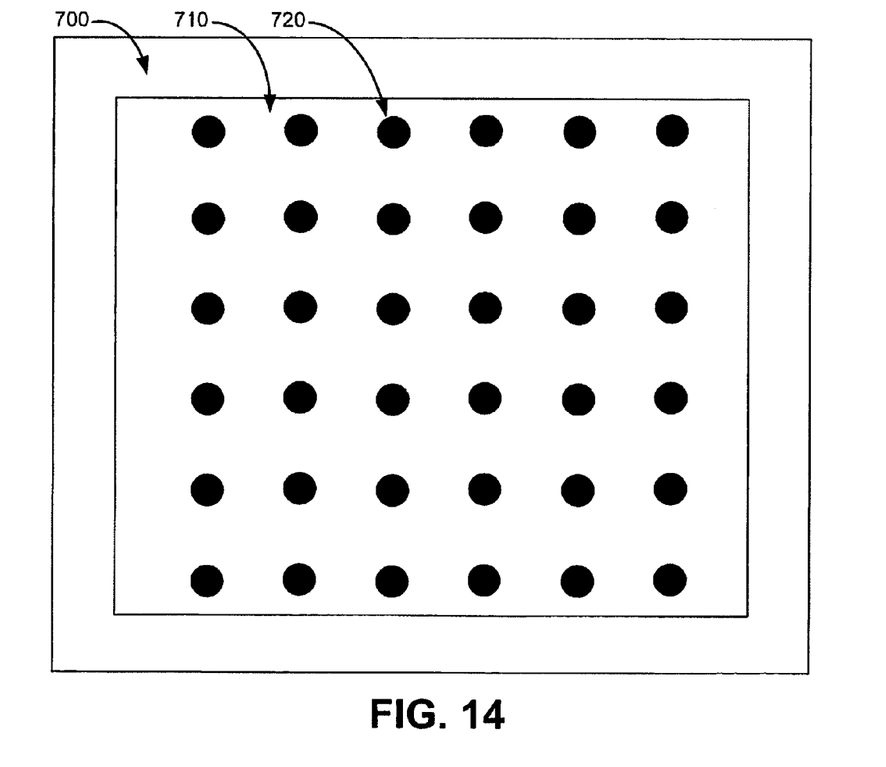
FIG. 14 is a diagram of an embodiment of a display device depicting a representative image for suppressing motion sickness using a scene dot-pattern overlay.
Figure 15:
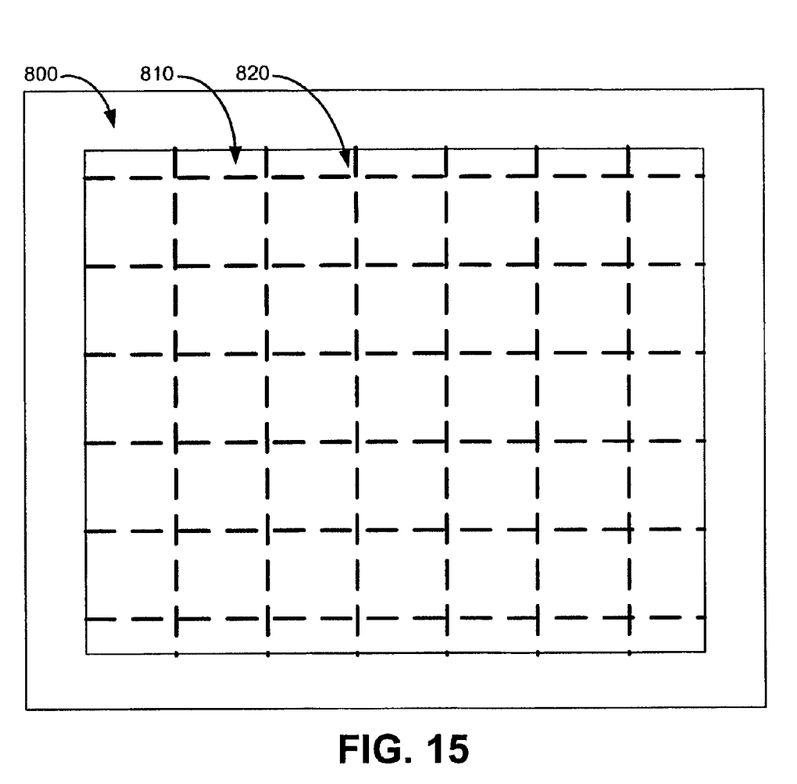
FIG. 15 is a diagram of an embodiment of a display device depicting a representative image for suppressing motion sickness using a scene line grid overlay.

For higher amplitudes within the motion sickness frequency range, it may be necessary to provide an additional compensatory display that is overlaid on the scene itself. Reference is now made to FIG. 14, illustrating a display 700 with a dot pattern 720 overlaid on the scene 710 for this purpose. The pattern is moved in synchronization with the peripheral displays. Similarly, FIG. 15 illustrates a stronger reinforcement consisting of a line grid overlay 820 for the scene 810. In this embodiment, the additional compensation is provided by a grid pattern consisting of an array of dots forming intersecting lines, with the line dot density being varied from sparse to solid with increasing vibration amplitudes.

In addition to the above embodiments for application to vehicle cab-mounted panel displays, these methods may alternatively be applied to head mounted displays. As applied to a head mounted display, the compensatory displays may be in an annular ring peripherally located about the central scene display and the display sensor may be head mounted. The operator is always looking at the scene display and the intensity of the compensatory display elements is a function of the acceleration discrepancy power spectrum.

When a system for suppressing motion sickness is implemented in software, it should be noted that the system can be stored on any computer-readable medium for use by or in connection with any computer-related system or method. In the context of this document, a computer-readable medium is an electronic, magnetic, optical, or other physical device or means that can contain or store a computer program for use by or in connection with a computer-related system or method. More specific examples (a nonexhaustive list) of the computer-readable medium would include the following: an electrical connection (electronic) having one or more wires, a portable computer diskette (magnetic), a random access memory (RAM) (electronic), a read-only memory (ROM) (electronic), an erasable programmable read-only memory (EPROM, EEPROM, or Flash memory) (electronic), an optical fiber (optical), and a portable compact disc read-only memory (CDROM) (optical). Note that the computer-readable medium could even be paper or another suitable medium upon which the program is printed, as the program can be electronically captured, via for instance optical scanning of the paper or other medium, then compiled, interpreted or otherwise processed in a suitable manner if necessary, and then stored in a computer memory.

It should be emphasized that many variations and modifications may be made to the above-described embodiments. For instance, as disclosed above, the compensatory images can change size to compensate for accelerations relative to the z-axis of the coordinate system. That is, scene images accelerating forward faster than the vehicle can result in compensatory images decreasing in size. Also, as disclosed above, compensatory images can additionally or alternatively change color, shape and intensity in response to the compensatory velocity, $V_C$.

All such modifications and variations are intended to be included herein within the scope of this disclosure and protected by the following claims.

What is claimed is:

1. A system for suppressing motion sickness, said system comprising:
    a display device operative to display a first image and a second image;
    a display controller communicating with the display device and operative to control display of the second image such that the second image moves relative to the display device in response to at least one of: motion of the first image relative to the display device, and motion of the display device;
    an image motion sensor operative to determine motion of the first image relative to the display device from a velocity flow field of the first image and from a viewing distance of a viewer, the image motion sensor providing information corresponding to motion of the first image to the display controller;
    a display motion sensor operative to determine motion of the display device, the display motion sensor providing information corresponding to the motion of the display device to the display controller;
    wherein the display controller comprises;
    a compensatory image engine operative to determine a second image composite motion based on both the motion of the first image relative to the display device and the motion of the display device;
    wherein the second image is a discrete simple geometric figure which is changed in accordance with the movement speed and direction of the second image.

2. The system of claim 1, wherein:
    the display device has a scene field for displaying the first image; and
    the second image is displayed outside of the scene field.

3. The system of claim 2, wherein the display device has a compensatory field for displaying the second image, at least a portion of the compensatory field being located adjacent to an outer edge of the scene field.

4. The system of claim 3, wherein the compensatory field surrounds the scene field.

5. The system of claim 1, wherein the second image comprises a morphologic variation of a circle the form of which is changed in accordance with the movement speed and direction of the second image;
    wherein the second image comprises a size, the value of which is changed in accordance with the movement speed and direction of the second image;
    wherein the second image comprises color hue and saturation intensity, the values of which are changed in accordance with the movement speed and direction of the second image;
    wherein the changes of the form, size, color hue and saturation intensity comprise a synchronized manner in accordance with the movement speed and direction of the second image.

6. The system of claim 5, wherein the second image is a circle or morphologic variations in the form thereof, constituting at least one of a circle, ellipse, elongated ellipse, cusp, sector, or a chevron, in accordance with the movement speed and direction of the second image.

7. The system of claim 6, wherein the second image comprises a morphologic variation of a chevron the form of which is changed in accordance with the movement speed and direction of the second image; wherein the chevron has an apex, the apex pointed generally in a direction of motion of the second image; wherein the chevron has an included angle, the included angle decreased as a speed of the second image with respect to the display device increases, and increased as the speed of the second image decreases.

8. The system of claim 5, wherein the second image comprises an increasing size, brighter intensity, and reddish hue during acceleration, and the second image decreasing size, decreased intensity, and bluish hue during de-acceleration.

9. The system of claim 1, wherein:
the compensatory image engine further comprises a means of determining a compensatory velocity flow field for the second image; and
the second image comprises separation into frames each of which displays separate multiple second image in accordance with the movement speed and direction of the compensatory velocity flow field.

10. The system of claim 9, wherein: the second image comprises one of multiple second images; wherein as the velocity flow of the second images changes, a spacing between the second images is changed in accordance.

11. A method for suppressing motion sickness in a viewer of a display device, the display device displaying a first image, said method comprising:
determining a motion component of the first image from changes in a velocity flow field of the image, and from a viewing distance of a viewer;
displaying a second image to the user, the second image moving generally counter to a composite motion, the composite motion comprising a first component corresponding to the motion of the first image, and a second component corresponding to a motion of the display device; and
displaying the second image as a discrete simple geometric figure which is changed in accordance with a movement speed and direction of the second image.

12. The method of claim 11, wherein: the display device displays the first image within a scene field; and the second image is displayed outside the scene field.

13. The method of claim 11, wherein the second image is a morphologic variation of a circle the form of which is changed in accordance with the movement speed and direction of the second image;
wherein the second image has a size, the value of which is changed in accordance with the movement speed and direction of the second image;
wherein the second image has a color hue and saturation intensity, the values of which are changed in accordance with the movement speed and direction of the second image; and
wherein the second image has an apex, the apex pointing generally in a direction of motion of the second image; and
wherein the form, size, color hue and saturation intensity are changed in a synchronous manner in accordance with the movement speed and direction of the second image.

14. The method of claim 13, wherein the second image displays an increasing size, brighter intensity, and reddish hue during acceleration, and the second image decreasing size, decreased intensity, and bluish hue during de-acceleration.

15. The method 13, wherein the second image is a morphologic variation of a circle constituting at least one of a circle, ellipse, elongated ellipse, cusp, sector, or chevron, in accordance with the movement speed and direction of the second image.

16. The method of claim 11, wherein the method further consists of:
determining a compensatory velocity flow field for the second image; and
separating the second image into frames each of which displays separate multiple second images in accordance with the movement speed and direction of the compensatory velocity flow field.

17. A method for suppressing motion sickness in a viewer of a display device, the display device displaying a first image, said method comprising:
displaying a second image to the user, the second image moving relative to the display device in a manner corresponding to at least one of: motion of the first image relative to the display device, and motion of the display device;
wherein the display device displays the first image within a scene field; and the second image is displayed outside the scene field;
wherein the second image is a chevron having an apex, the apex pointing generally in a direction of motion of the second image;
wherein the chevron has an included angle, the included angle decreasing as a speed of the second image with respect to the display device increases, and increasing as the speed of the second image decreases.

18. A method for suppressing motion sickness in a viewer of a display device, the display device displaying a first image, said method comprising:
displaying a second image to the user, the second image moving relative to the display device in a manner corresponding to at least one of: motion of the first image relative to the display device, and motion of the display device;
wherein the display device displays the first image within a scene field; and the second image is displayed outside the scene field;
wherein the second image is one of multiple second images;
wherein as a velocity flow of the second images changes, a spacing between the second images changes in accordance.

* * * * *